(12) United States Patent
Ganss et al.

(10) Patent No.: US 10,596,301 B2
(45) Date of Patent: Mar. 24, 2020

(54) DEVICE INCLUDING BIOLOGICAL AGENTS FOR IN VITRO INDUCTION OF BIOMINERALIZATION

(71) Applicant: THE GOVERNING COUNCIL OF THE UNIVERSITY OF TORONTO, Toronto (CA)

(72) Inventors: Bernhard Ganss, Toronto (CA); Yuichi Ikeda, Tokyo (JP)

(73) Assignee: THE GOVERNING COUNCIL OF THE UNIVERSITY OF TORONTO, Toronto, ON (CA)

( * ) Notice: Subject to any disclaimer, the term of this patent is extended or adjusted under 35 U.S.C. 154(b) by 0 days.

(21) Appl. No.: 15/988,914

(22) Filed: May 24, 2018

(65) Prior Publication Data
US 2019/0030213 A1 Jan. 31, 2019

Related U.S. Application Data

(60) Provisional application No. 62/511,643, filed on May 26, 2017.

(51) Int. Cl.
*A61L 27/54* (2006.01)
*A61L 27/26* (2006.01)
(Continued)

(52) U.S. Cl.
CPC .............. *A61L 27/54* (2013.01); *A61L 27/24* (2013.01); *A61L 27/26* (2013.01); *A61L 27/34* (2013.01);
(Continued)

(58) Field of Classification Search
CPC ........ A61K 27/54; A61K 27/56; A61K 27/24; A61K 27/34; A61K 27/52; A61K 27/26; A61L 27/54; A61L 27/56; A61L 27/24; A61L 27/34; A61L 27/52; A61L 27/26; A61L 2430/02; A61L 2300/252; A61L 2430/12

See application file for complete search history.

(56) References Cited

PUBLICATIONS

Iwasaki et al, Amelotin—A Novel Secreted Ameloblast-Specific Protein, J Dent Res, 84(12): 1127-1132 (Year: 2005).*

(Continued)

*Primary Examiner* — Carlos A Azpuru
(74) *Attorney, Agent, or Firm* — Hill & Schumacher

(57) ABSTRACT

This disclosure provides a product comprised of a collagen gel to which recombinant human Amelotin (AMTN) protein is added. This AMTN-collagen gel is applied to one side of a physiologically acceptable scaffold that has first been impregnated with AMTN-free collagen gel. The resulting two-layer collagen membrane (layer 1 comprised of scaffold surrounded by collagen gel; layer 2 comprised of collagen gel containing AMTN) is applied to a mineralized tissue surface such as dentin and bone with the collagen gel containing AMTN of layer 2 facing this mineral surface. Upon immersion in simulated body fluid (SBF), the presence of AMTN in layer 2 triggers the formation of hydroxyapatite mineral deposits that intimately connect with the existing mineral surface and thus provide physical attachment. A similar product is disclosed but in addition to AMTN, it contains the Odontogenic, Ameloblast-Associated (ODAM) protein as well with both proteins exhibiting a synergistic effect.

15 Claims, 15 Drawing Sheets
Specification includes a Sequence Listing.

(51) Int. Cl.
A61L 27/52 (2006.01)
A61L 27/56 (2006.01)
A61L 27/24 (2006.01)
A61L 27/34 (2006.01)

(52) U.S. Cl.
CPC .............. A61L 27/52 (2013.01); A61L 27/56 (2013.01); A61L 2300/252 (2013.01); A61L 2430/02 (2013.01); A61L 2430/12 (2013.01)

(56) References Cited

PUBLICATIONS

Iwasaki, K., et al. Amelotin—a Novel Secreted, Ameloblast-specific Protein. Journal of dental research 84, 1127-1132 (2005).
Seguier, S., Godeau, G. & Brousse, N. Collagen fibers and inflammatory cells in healthy and diseased human gingival tissues: a comparative and quantitative study by immunohistochemistry and automated image analysis. J Periodontol 71, 1079-1085 (2000).
Bassani, D.G., Olinto, M.T. & Kreiger, N. Periodontal disease and perinatal outcomes: a case- control study. J Clin Periodontol 34, 31-39 (2007).
Braegger, U. Cost-benefit, cost-effectiveness and cost-utility analyses of periodontitis prevention. J Clin Periodontol 32 Suppl 6, 301-313 (2005).
Overall, C.M., Sodek, J., McCulloch, C.A. & Birek, P. Evidence for polymorphonuclear leukocyte collagenase and 92-kilodalton gelatinase in gingival crevicular fluid. Infect Immun 59, 4687-4692 (1991).
Lee, W., et al. Collagenase activity in recurrent periodontitis: relationship to disease progression and doxycycline therapy. J Periodontal Res 26, 479-485 (1991).
Ripamonti, U. & Renton, L. Bone morphogenetic proteins and the induction of periodontal tissue regeneration. Periodontol 2000 41, 73-87 (2006).
Stavropoulos, A. & Wikesjo, U.M. Growth and differentiation factors for periodontal regeneration: a review on factors with clinical testing. J Periodontal Res 47, 545-553 (2012).
Love, R.M. & Jenkinson, H.F. Invasion of dentinal tubules by oral bacteria. Crit Rev Oral Biol Med 13, 171-183 (2002).
Bogle, G., Adams, D., Crigger, M., Klinge, B. & Egelberg, J. New attachment after surgical treatment and acid conditioning of roots in naturally occurring periodontal disease in dogs. J Periodontal Res 16, 130-133 (1981).
Selvig, K.A., Ririe, C.M., Nilveus, R. & Egelberg, J. Fine structure of new connective tissue attachment following acid treatment of experimental furcation pockets in dogs. J Periodontal Res 16, 123-129 (1981).
Pontoriero, R., et al. Guided tissue regeneration in degree II furcation-involved mandibular molars. A clinical study. J Clin Periodontol 15, 247-254 (1988).
Wang, Q., Downey, G.P. & McCulloch, C.A. Focal adhesions and Ras are functionally and spatially integrated to mediate IL-1 activation of ERK. FASEB journal: official publication of the Federation of American Societies for Experimental Biology 25, 3448-3464 (2011).
Jung, R.E., Hurzeler, M.B., Thoma, D.S., Khraisat, A. & Hammerle, C.H. Local tolerance and efficiency of two prototype collagen matrices to increase the width of keratinized tissue. J Clin Periodontol 38, 173-179.
Lee, C.K., et al. Biological effects of a porcine-derived collagen membrane on intrabony defects. J Periodontal Implant Sci 40, 232-238.
Bornstein, M.M., Bosshardt, D. & Buser, D. Effect of two different bioabsorbable collagen membranes on guided bone regeneration: a comparative histomorphometric study in the dog mandible. J Periodontol 78, 1943-1953 (2007).
Sculean, A., et al. Healing of intrabony defects following treatment with a bovine-derived xenograft and collagen membrane. A controlled clinical study. J Clin Periodontol 30, 73-80 (2003).
Lee, W., Sodek, J. & McCulloch, C.A. Role of integrins in regulation of collagen phagocytosis by human fibroblasts. J Cell Physiol 168, 695-704 (1996).
Moffatt, P., et al. Cloning of rat amelotin and localization of the protein to the basal lamina of maturation stage ameloblasts and junctional epithelium. The Biochemical journal 399, 37-46 (2006).
Somogyi-Ganss, E., et al. Comparative temporospatial expression profiling of murine amelotin protein during amelogenesis. Cells Tissues Organs 195, 535-549 (2012).
Nishio, C., Wazen, R., Kuroda, S., Moffatt, P. & Nanci, A. Expression pattern of odontogenic ameloblast-associated and amelotin during formation and regeneration of the junctional epithelium. European cells & materials 20, 393-402 (2010).
Lacruz, R.S., et al. Targeted overexpression of amelotin disrupts the microstructure of dental enamel. PloS one 7, e35200 (2012).
Fisher, L.W., Torchia, D.A., Fohr, B., Young, M.F. & Fedarko, N.S. Flexible structures of Sibling proteins, bone sialoprotein, and osteopontin. Biochem Biophys Res Commun 280, 460-465 (2001).
Parry, D.A., et al. Mutations in C4orf26, encoding a peptide with in vitro hydroxyapatite crystal nucleation and growth activity, cause amelogenesis imperfecta. American journal of human genetics 91, 565-571 (2012).
McCulloch, C.A. Effect of experimental periodontitis on fibroblast progenitor populations in hamster gingiva. J Periodontal Res 21, 685-691 (1986).
Nayak, B.N., et al. Healing of periodontal tissues following transplantation of cells in a rat orthodontic tooth movement model. The Angle orthodontist 78, 826-831 (2008).
Nemeth, E., Kulkarni, G.W. & McCulloch, C.A. Disturbances of gingival fibroblast population homeostasis due to experimentally induced inflammation in the cynomolgus monkey (*Macaca fascicularis*): potential mechanism of disease progression. J Periodontal Res 28, 180-190 (1993).
Birek, P., McCulloch, C.A. & Overall, C.M. Measurements of probing velocity with an automated periodontal probe and the relationship with experimental periodontitis in the Cynomolgus monkey (*Macaca fascicularis*). Arch Oral Biol 34, 793-801 (1989).
Tessier, J.F., Ellen, R.P., Birek, P., Kulkarni, G.V. & McCulloch, C.A. Relationship between periodontal probing velocity and gingival inflammation in human subjects. J Clin Periodontol 20, 41-48 (1993).
McCulloch, C.A., et al. Randomized controlled trial of doxycycline in prevention of recurrent periodontitis in high-risk patients: antimicrobial activity and collagenase inhibition. J Clin Periodontol 17, 616-622 (1990).
O'Brien-Simpson, N.M., et al. Role of RgpA, RgpB, and Kgp proteinases in virulence of Porphyromonas gingivalis W50 in a murine lesion model. Infect Immun 69, 7527-7534 (2001).
Kilian, M., Frandsen, E.V., Haubek, D. & Poulsen, K. The etiology of periodontal disease revisited by population genetic analysis. Periodontol 2000 42, 158-179 (2006).
Mancini, S., et al. Assessment of a novel screening test for neutrophil collagenase activity in the diagnosis of periodontal diseases. J Periodontol 70, 1292-1302 (1999).
Sone, E.D. & Stupp, S.I. Bioinspired magnetite mineralization of peptide-amphiphile nanofibers. Chem Mater 23, 2005-2007 (2011).
Oyane, A., et al. Preparation and assessment of revised simulated body fluids. Journal of biomedical materials research. Part A 65, 188-195 (2003).
Aoba, T. & Moreno, E.C. The enamel fluid in the early secretory stage of porcine amelogenesis: chemical composition and saturation with respect to enamel mineral. Calcified tissue international 41, 86-94 (1987).
Habelitz, S., Marshall, G.W., Jr., Balooch, M. & Marshall, S.J. Nanoindentation and storage of teeth. Journal of biomechanics 35, 995-998 (2002).
Lausch. A.J., Quan, B.D., Miklas, J.W. & Sone, E.D. Extracellular matrix control of collagen mineralization in vitro. Adv. Funct. Mater. DOI: 10.1002/adfm.201203760(2013).
Sone, E.D. & Quan, B.D. Structure of the collagen fibril across a mineralized interface: A cryo-TEM study of the periodontal ligament-cememtum junction. Microscopy and Microanalysis 18 (Suppl. 2), 1590-1591 (2012).

(56) References Cited

PUBLICATIONS

Dickgreber, N., et al. Targeting antigen to MHC class II molecules promotes efficient cross-presentation and enhances immunotherapy. Journal of immunology 182, 1260-1269 (2009).

Park, J.S., Lee, W. & McCulloch, C.A. Intercellular transfer of apoptotic signals via electrofusion. Exp Cell Res 318, 896-903.

Socransky, S.S., Haffajee, A.D., Goodson, J.M. & Lindhe, J. New concepts of destructive periodontal disease. J Clin Periodontol 11, 21-32 (1984).

Baker, P.J., Dixon, M. & Roopenian, D.C. Genetic control of susceptibility to Porphyromonas gingivalis-induced alveolar bone loss in mice. Infect Immun 68, 5864-5868 (2000).

Okada, Y., et al. Blockade of sympathetic b-receptors inhibits Porphyromonas gingivalis-induced alveolar bone loss in an experimental rat periodontitis model. Arch Oral Biol 55, 502-508 (2010).

Hamada, N., et al. The r40-kDa outer membrane protein human monoclonal antibody protects against Porphyromonas gingivalis-induced bone loss in rats. J Periodontol 78, 933-939 (2007).

Kesavalu, L., et al. Rat model of polymicrobial infection, immunity, and alveolar bone resorption in periodontal disease. Infect Immun 75, 1704-1712 (2007).

Lekic, P., Sodek, J. & McCulloch, C.A. Relationship of cellular proliferation to expression of osteopontin and bone sialoprotein in regenerating rat periodontium. Cell Tissue Res 285, 491-500 (1996).

Lekic, P., Sodek, J. & McCulloch, C.A. Osteopontin and bone sialoprotein expression in regenerating rat periodontal ligament and alveolar bone. Anat Rec 244, 50-58 (1996).

Rajshankar, D., McCulloch, C.A., Tenenbaum, H.C. & Lekic, P.C. Osteogenic inhibition by rat periodontal ligament cells: modulation of bone morphogenic protein-7 activity in vivo. Cell Tissue Res 294, 475-483 (1998).

Lekic, P.C., Rajshankar, D., Chen, H., Tenenbaum, H. & McCulloch, C.A. Transplantation of labeled periodontal ligament cells promotes regeneration of alveolar bone. Anat Rec 262, 193-202 (2001). 57. Chano, L., Tenenbaum.

Chano, L., Tenenbaum, H.C., Lekic, P.C., Sodek, J. & McCulloch, C.A. Emdogain regulation of cellular differentiation in wounded rat periodontium. J Periodontal Res 38, 164-174 (2003).

Martuscelli, G., Fiorellini, J.P., Crohin, C.C. & Howell, T.H. The effect of interleukin-11 on the progression of ligature-induced periodontal disease in the beagle dog. J Periodontol 71, 573-578 (2000).

Rajshankar, D., et al. Role of PTPalpha in the Destruction of Periodontal Connective Tissues. PLoS One, vol. 8 (Issue 8), e70659. Published Aug. 5, 2013.

Stolf, D.P., Lee, T.-Y., Bradley, G. & Ganss, B. Evaluation of Amelotin Expression in Benign Odontogenic Tumors. J Interdiscipl Histopathol 2013; 1 (5); pp. 236-245 doi: 10.5455/jihp. 20130506045106 Published May 11, 2013.

\* cited by examiner

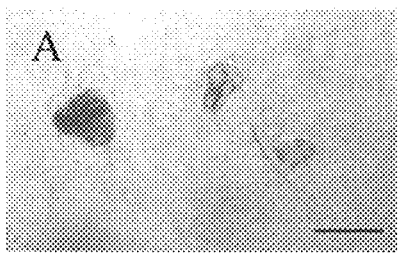
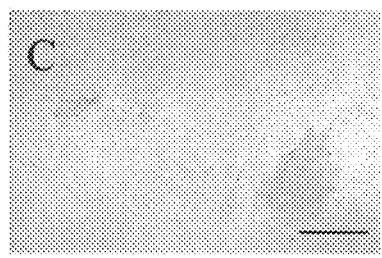
FIG. 1A  FIG. 1B  FIG. 1C
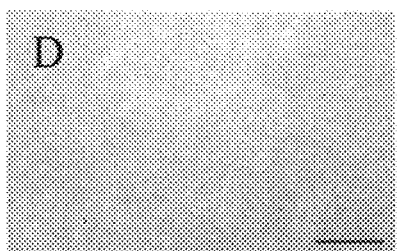
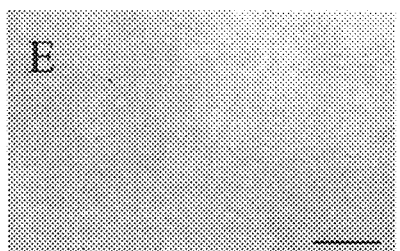
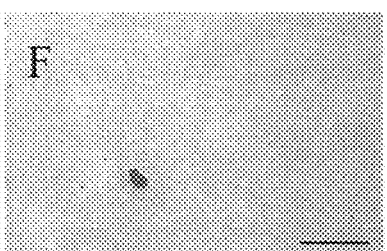
FIG. 1D  FIG. 1E  FIG. 1F

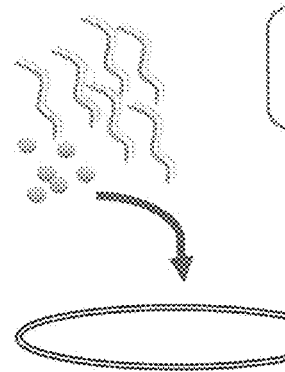
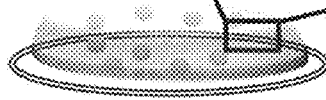
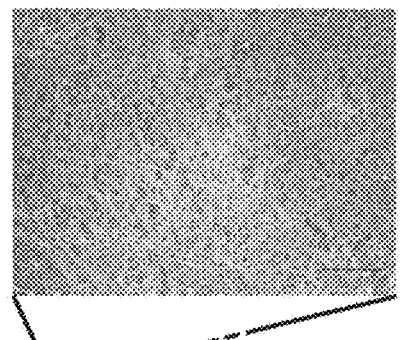
FIG. 3Aa
FIG. 3Ab rhAMTN-impregnated Collagen Gel Collagen Gel 5 hours 24 hours Magnification   x40                x2000              x15000 rhAMTN

PBS

Control

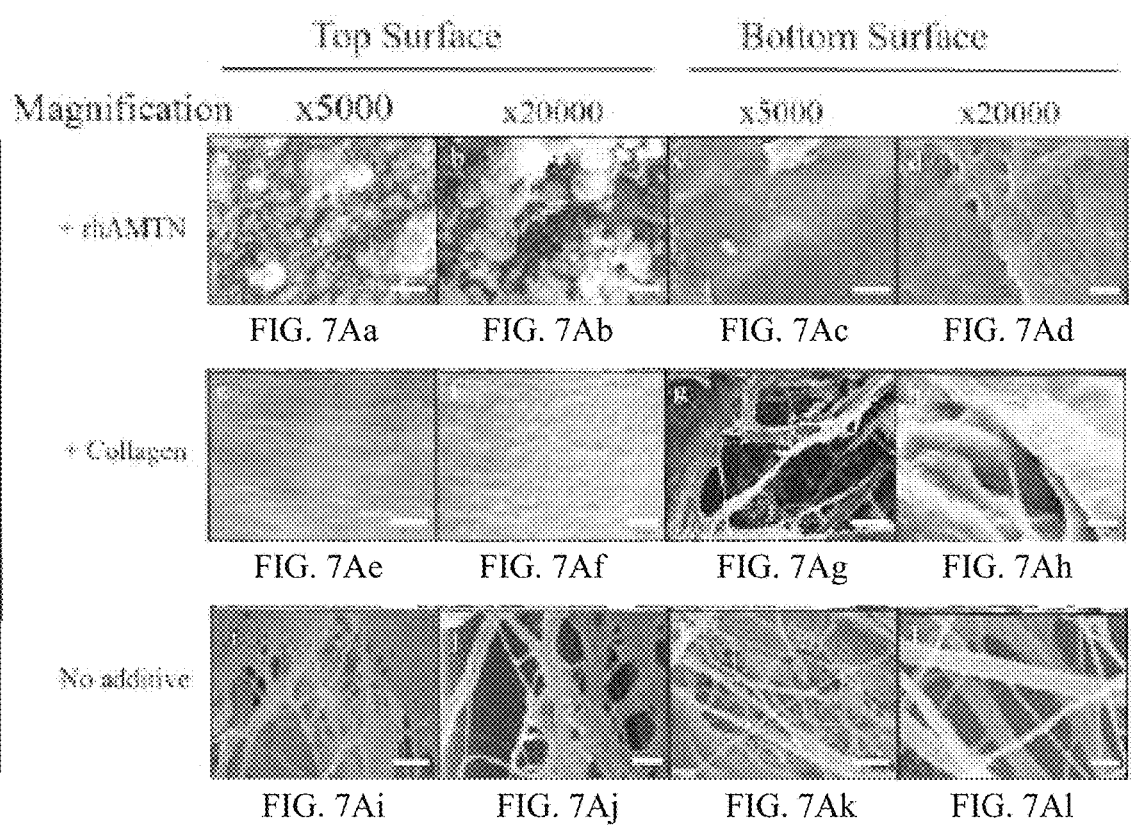

FIG. 7Ba Top Side
FIG. 7Bb Middle
FIG. 7Bc Bottom Side
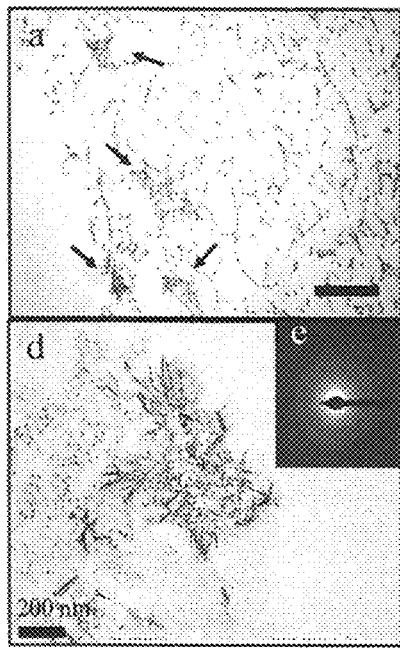
FIG. 7Bd
FIG. 7Be
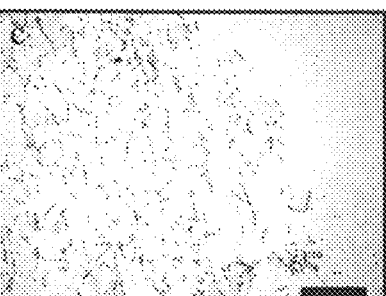

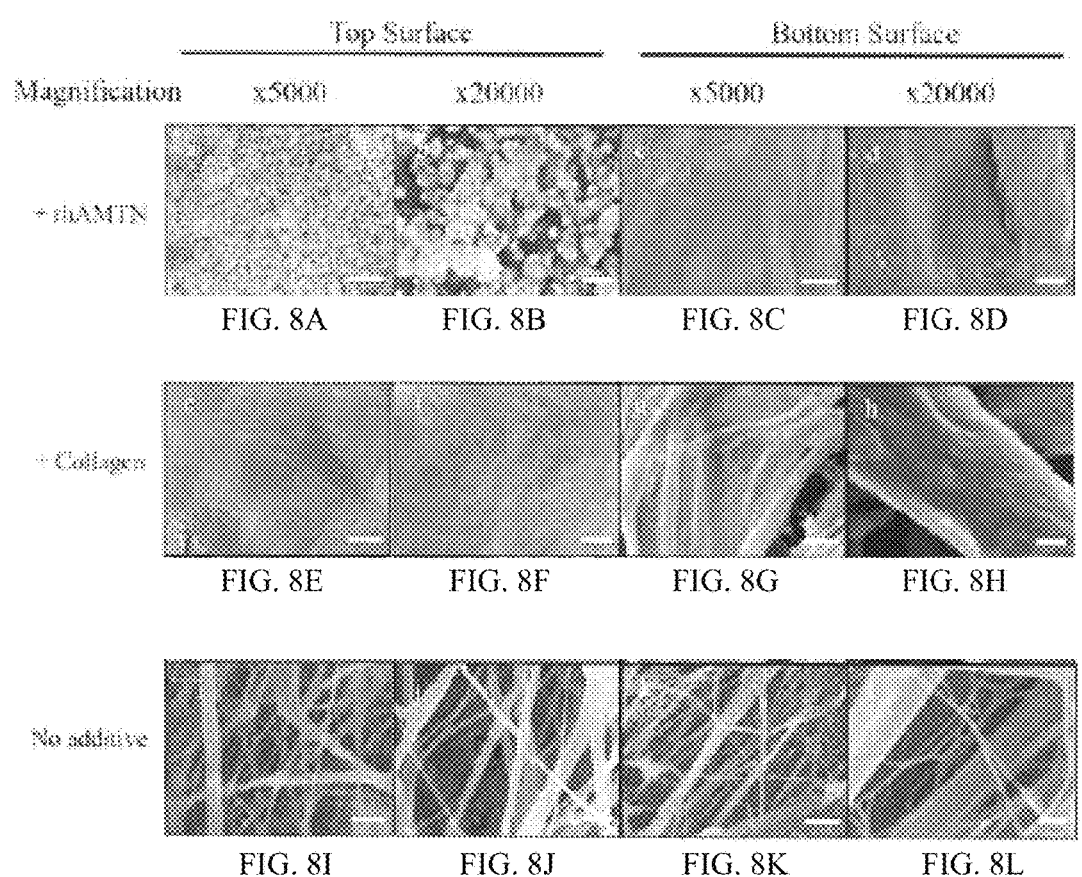

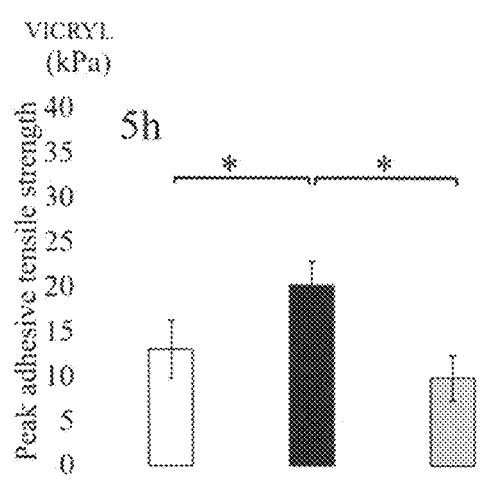 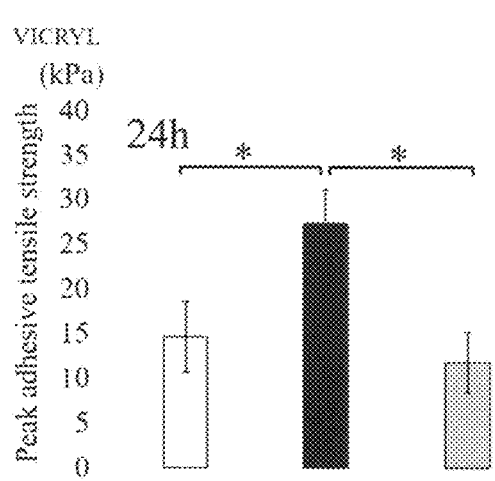
FIG. 10A                     FIG. 10B 5 hours
| | Magnification | Top Surface | | Bottom Surface | |
|---|---|---|---|---|---|
| | | x5000 | x20000 | x5000 | x20000 |
| VICRYL + rhAMTN | | FIG. 11Aa | FIG. 11Ab | FIG. 11Ac | FIG. 11Ad |
| VICRYL + Collagen | | FIG. 11Ae | FIG. 11Af | FIG. 11Ag | FIG. 11Ah |
| VICRYL No additive | | FIG. 11Ai | FIG. 11Aj | FIG. 11Ak | FIG. 11Al |
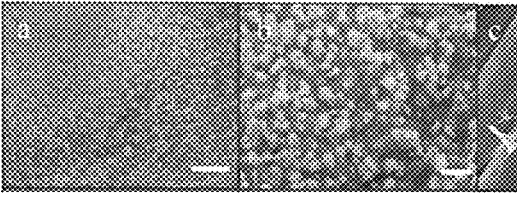

24 hours
| | Top Surface | | Bottom Surface | |
|---|---|---|---|---|
| Magnification | x5000 | x20000 | X5000 | x20000 |
VICRYL
+ rhAMTN
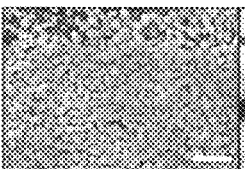 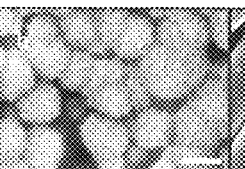 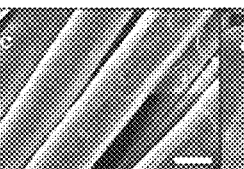 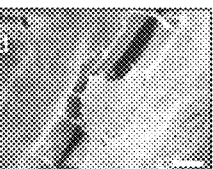
FIG. 11Ba　　FIG. 11Bb　　FIG. 11Bc　　FIG. 11Bd
+ Collagen
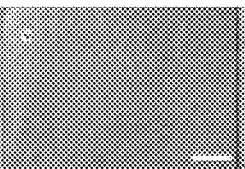 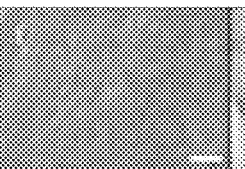 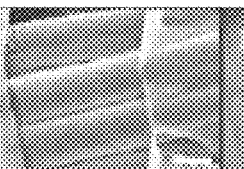 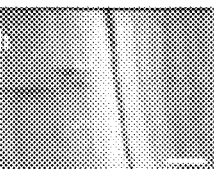
FIG. 11Be　　FIG. 11Bf　　FIG. 11Bg　　FIG. 11Bh
No additive
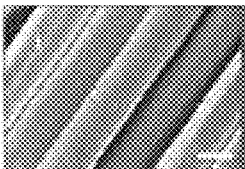 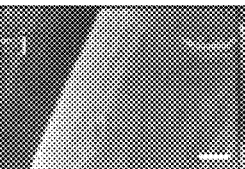 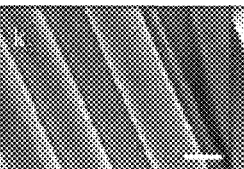 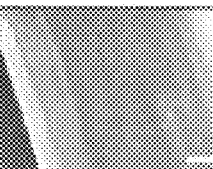
FIG. 11Bi　　FIG. 11Bj　　FIG. 11Bk　　FIG. 11Bl

SEQUENCE LISTING

```
<160> NUMBER OF SEQ ID NOS: 12

<210> SEQ ID NO 1
<211> LENGTH: 20
<212> TYPE: DNA
<213> ORGANISM: Mus musculus

<400> SEQUENCE: 1
gagcggagag tactggatcg                                                   20

<210> SEQ ID NO 2
<211> LENGTH: 20
<212> TYPE: DNA
<213> ORGANISM: Mus musculus

<400> SEQUENCE: 2
tactcgaacg ggaatccatc                                                   20

<210> SEQ ID NO 3
<211> LENGTH: 20
<212> TYPE: DNA
<213> ORGANISM: Mus musculus

<400> SEQUENCE: 3
gggaggcagt gactcttcag                                                   20

<210> SEQ ID NO 4
<211> LENGTH: 20
<212> TYPE: DNA
<213> ORGANISM: Mus musculus

<400> SEQUENCE: 4
tcgtcgcttt ccttcacttt                                                   20

<210> SEQ ID NO 5
<211> LENGTH: 20
<212> TYPE: DNA
<213> ORGANISM: Mus musculus

<400> SEQUENCE: 5
gcgctctgtc tctctgacct                                                   20

<210> SEQ ID NO 6
<211> LENGTH: 20
<212> TYPE: DNA
```

```
<213> ORGANISM: Mus musculus

<400> SEQUENCE: 6
gcggtcttca agccatactg                                                    20

<210> SEQ ID NO 7
<211> LENGTH: 20
<212> TYPE: DNA
<213> ORGANISM: Mus musculus

<400> SEQUENCE: 7
tcctcggttc tctccatctg                                                    20

<210> SEQ ID NO 8
<211> LENGTH: 20
<212> TYPE: DNA
<213> ORGANISM: Mus musculus

<400> SEQUENCE: 8
tgcaggagag aggagtccat                                                    20

<210> SEQ ID NO 9
<211> LENGTH: 20
<212> TYPE: DNA
<213> ORGANISM: Mus musculus

<400> SEQUENCE: 9
ggggacatgc agtatgaatt                                                    20

<210> SEQ ID NO 10
<211> LENGTH: 20
<212> TYPE: DNA
<213> ORGANISM: Mus musculus

<400> SEQUENCE: 10
ggcctggtag ttgttgtgag                                                    20

<210> SEQ ID NO 11
<211> LENGTH: 20
<212> TYPE: DNA
<213> ORGANISM: Mus musculus

<400> SEQUENCE: 11
aactttggca ttgtggaagg                                                    20

<210> SEQ ID NO 12
<211> LENGTH: 20
<212> TYPE: DNA
<213> ORGANISM: Mus musculus

<400> SEQUENCE: 12
acacattggg ggtaggaaca                                                    20
```

DEVICE INCLUDING BIOLOGICAL AGENTS FOR IN VITRO INDUCTION OF BIOMINERALIZATION

FIELD

The present disclosure relates to biological agents for inducing biomineralization in dental therapy. More particularly the present disclosure relates to biocompatible membranes incorporating these biological agents.

BACKGROUND

The integrity of interfaces between soft and mineralized tissues is crucial to the functionality of tendons and ligaments in joints and the periodontal ligament. While several synthetic approaches such as inorganic "bone cement" formulations and polyurethane-based materials are being developed for the fixation of detached tissues in bones, the translation into commercial products for clinical use has not been realized. In the specific case of the periodontal ligament, which attaches the tooth to the jaw bone, no current technology is available to re-establish this attachment when lost in pathological conditions (periodontal disease). One specific problem in re-establishing periodontal attachment is the propensity of the gingival epithelial (GE) tissue to proliferate rapidly and grow along the mineralized tooth surface without establishing a functional attachment.

Being able to find a means to re-establish periodontal attachment while avoiding the proliferation of gingival epithelial (GE) tissue would facilitate periodontal attachment.

SUMMARY

The product of the present disclosure is based on the discovery that when certain biological agent(s), when placed in an appropriate carrier, is (are) able to induce the formation of mineral and thus attachment directly on the tooth surface, thereby excluding GE cells while the periodontal tissue regenerates. Specifically the inventors have discovered that the enamel proteins Amelotin (AMTN) and Odontogenic and Ameloblast-Associated (ODAM), when, alone or in combination, are embedded into collagen gels were able to induce the formation of hydroxyapatite crystals in a dose-dependent manner, most effectively on the surface and to a lesser degree in the interior, of collagen gels. AMTN alone induced the formation of mineral deposits after 5 hours, while mineral formation was first observed after 24 hours with ODAM. The combination of AMTN and ODAM induced mineralization in a synergistic manner. The mineralized deposits were characterized as hydroxyapatite.

Studies show that AMTN and ODAM are able to maintain their mineral-inducing properties in a type I collagen matrix that is the major organic constituent of all other HA-based mineralized tissues such as bone and dentin. The studies show that AMTN and ODAM-induced minerals are able to mediate physical attachment to mineralized tissue.

This disclosure provides a product comprised of a collagen gel, prepared from commercial sources, to which recombinant human AMTN protein (expressed in $E.\ coli$) is added. This AMTN-collagen gel is applied to one side of commercially available scaffolds (e.g. Vicryl mesh or Cytoplast collagen membranes) that have been impregnated with AMTN-free collagen gel. The resulting two-layer collagen membrane (layer 1 comprised of scaffold surrounded by collagen gel; layer 2 comprised of collagen gel containing AMTN) is applied to a mineralized tissue surface (e.g. dentin, bone) with the collagen gel containing AMTN of layer 2 facing this mineral surface. Upon immersion in simulated body fluid (SBF), the presence of AMTN in layer 2 triggers the formation of hydroxyapatite mineral deposits that intimately connect with the existing mineral surface and thus provide physical attachment.

A similar product, but instead of AMTN, the ODAM protein (also expressed in $E.\ coli$) was used and it too was observed to form hydroxyapatite mineral deposits that intimately connect with the existing mineral surface and thus provide physical attachment, albeit on a longer time scale than the AMTN product. Thus products containing both proteins also formed hydroxyapatite mineral deposits that intimately connect with the existing mineral surface and thus provide physical attachment. The combination of AMTN and ODAM induced mineralization in a synergistic manner. The mineralized deposits were characterized as hydroxyapatite. These in vitro results indicate that the enamel proteins AMTN and ODAM are able to synergistically induce hydroxyapatite mineralization outside of their natural biological matrix context.

Thus, the present disclosure provides a device for in vitro induction of biomineralization, comprising:
  a) a physiologically acceptable porous scaffold;
  b) said porous scaffold being impregnated with a first layer of collagen gel;
  c) a second collagen layer located on top of the first layer, said second layer including a mixture of collagen and Amelotin protein (AMTN); and
  d) wherein in use said device is configured to be applied with said second layer with the mixture of collagen gel containing Amelotin protein in physical contact with a mineralized tissue surface, the device being characterized in that a presence of Amelotin protein in the second layer triggers the formation of hydroxyapatite mineral deposits that intimately connect the second layer with the mineralized tissue surface and thus provide physical attachment.

The Amelotin protein may be present in the second layer in an amount from about 5 to about 25% % by wt. in collagen solution.

The Amelotin protein may be present in the second layer is an amount from about 10 to about 20% by wt. in collagen solution.

The present disclosure further provides a device for in vitro induction of biomineralization, comprising:
  a) a physiologically acceptable porous scaffold;
  b) said porous scaffold being impregnated with a first layer of collagen gel;
  c) a second layer located on top of the first layer, said second layer including a mixture of collagen, Amelotin (AMTN) protein and Odontogenic, Ameloblast-Associated (ODAM) protein; and
  d) wherein in use said device is configured to be applied with said second layer with the mixture of collagen gel containing AMTN and ODAM proteins in physical contact with a mineralized surface, the device being characterized in that a presence of AMTN and ODAM proteins in the second layer triggers the formation of hydroxyapatite mineral deposits that intimately connect the second layer with the mineralized surface and thus provide physical attachment.

The Amelotin protein may be present in the second layer in an amount from about 10 to about 20% by wt, and wherein the Odontogenic, Ameloblast-Associated protein is present in the second layer is an amount from about 15 to about 30% by wt.

The mineralized surface in the above devices may be a mineralized tissue surface. This mineralized tissue surface may be dentin or bone.

Alternatively, the mineralized surface may be one where the mineral is hydroxyapatite, and may be a calcium phosphate coated implant surface for dental or orthopedic implants.

The physiologically acceptable porous scaffold may be any one of Vicryl mesh, Cytoplast, porous collagen membranes, and mesh membranes.

A preferred physiologically acceptable porous scaffold is a collagen membrane.

To the best of the inventors knowledge, the use of AMTN and ODAM proteins, outside of their biological contexts, in a collagen matrix, resulting in mineral induction and physical attachment to mineralized tissues has never been observed before.

A further understanding of the functional and advantageous aspects of the present disclosure can be realized by reference to the following detailed description and drawings.

BRIEF DESCRIPTION OF THE DRAWINGS

Embodiments will now be described, by way of example only, with reference to the drawings, in which:

FIGS. 1A, 1B, 1C show Alizarin red stained MC3T3-E1 osteoblast cell cultures on day 10 supplemented with 100 μg/ml rh-AMTN in which Alizarin-red stained mineralized nodules are visible, Scale bar=0.5 mm. Images in FIGS. 1A, 1B and 1C are representative of three independent experiments, FIGS. 1D-1F show Alizarin red stained MC3T3-E1 osteoblast cell control cultures not supplemented with rh-AMTN. No visible mineralized nodules can be observed, Scale bar=0.5 mm. Images FIGS. 1D, 1E and 1F are representative of three independent experiments.

FIG. 3Aa shows a schematic diagram of making of rhAMTN-impregnated collagen gel in which collagen solution containing rhAMTN were put on the glass slide and incubated overnight in humidifier incubator at 37° C.

FIG. 3Ab shows a SEM image of the surface of rhAMTN-impregnated collagen gel, with scale bar=10 μm.

FIGS. 3Bc and 3Bd show TEM images of collagen samples incubated in the SBF buffer for 5 hours at 37° C. Calcium phosphate precipitates were seen on the surface and deeper into and embedded within the collagen gel (FIG. 3Ba). TEM (FIG. 3Bc) and SAED (FIG. 3Bd) analyses revealed that these precipitates have a hydroxyapatite crystalline structure (FIGS. 3Bc and 3Bd). Control gels with no AMTN incorporation contained no minerals (FIG. 3Bb).

FIGS. 7Aa to 7Al show SEM images of CYTOPLAST-rhAMTN membrane incubated in SBF buffer at 37° C. for 5 hours. Calcium phosphate precipitates were observed only on the top (AMTN-containing) surface of the CYTOPLAST-rhAMTN membrane (FIGS. 7Aa and 7Ab). No precipitate was observed on the bottom (AMTN-free) surface of the CYTOPLAST-rhAMTN membrane (FIGS. 7Ac and 7Ad), or on either surface of AMTN-free CYTOPLAST-Collagen membranes (FIGS. 7Ae to 7Ah) or CYTOPLAST membranes without collagen hydrogel or AMTN (FIGS. 7Ai to 7Al). Scale bar=10 and 2 μm.

FIGS. 7Ba to 7Be shows TEM images of CYTOPLAST-rhAMTN membrane incubated in the SBF buffer for 5 hours at 37° C. in which it can be seen from FIG. 7Ba that calcium phosphate precipitated only at top surface or top side of the membrane. The black arrows indicate the location of calcium phosphate precipitation. As can be seen from the higher magnification of FIGS. 7Bd and 7Be of the top side surface of the membrane, these precipitates had a needle-like hydroxyapatite crystalline structure. As can be seen from FIGS. 7Bb and 7Bc, no precipitate was observed in middle part or the bottom side of the membrane. Scale bar=1 μm and 200 nm.

FIG. 8 shows SEM images of CYTOPLAST-rhAMTN membrane incubated in SBF buffer at 37° C. for 24 hours. Calcium phosphate precipitates were observed on the top surface of CYTOPLAST-rhAMTN membrane (FIGS. 8A and 8B). No precipitate was observed in the bottom surface of CYTOPLAST-rhAMTN membrane (FIGS. 8C and 8D), or in both surfaces of CYTOPLAST-Collagen membrane (FIGS. 8E to 8H) and CYTOPLAST membrane with no additives (FIGS. 8I to 8L). Scale bar=10 and 2 μm.

FIGS. 10A and 10B show peak adhesive tensile strengths of VICRYL+rhAMTN membranes with dentin. Membranes were incubated in SBF buffer at 37° C. for 5 hours (FIG. 10A) and 24 hours (FIG. 10B), and then peak adhesive tensile strength between the dentin and the membrane was measured using the digital force gauge (white, VICRYL+Collagen membrane with 30% phosphoric acid treated dentin; black, CYTOPLAST+rhAMTN membrane with 30% phosphoric acid treated dentin; grey, CYTOPLAST+Collagen membrane with 30% phosphoric acid and rhAMTN treated dentin). Data was presented as mean±standard deviation; (*): mean significantly different between the groups with a one-way ANOVA with Tukey multiple comparison test (* p<0.05, n=3 experiments).

FIGS. 11Aa to 11Al show SEM images of VICRYL-rhAMTN membrane incubated in SBF buffer at 37° C. for 5 hours. Calcium phosphate precipitates are observed on the top surface of VICRYL-rhAMTN membrane (FIGS. 11Aa and 11Ab). No precipitate was observed in the bottom surface of AMTN-impregnated VICRYL membrane ((FIGS. 11Ac and 11Ad), in both surface of VICRYL membrane with collagen gel ((FIGS. 11Ae to 11Ah) and VICRYL membrane ((FIGS. 11Ai to 11Al). Scale bar=10 and 2 μm.

FIGS. 11Ba to 11Bl shows SEM images of VICRYL-rhAMTN membrane incubated in SBF buffer at 37° for 24 hours. Calcium phosphate precipitates are present on the top surface of VICRYL-rhAMTN membrane (FIGS. 11Aa and 11Bb). No precipitate was observed in the bottom surface of AMTN-impregnated VICRYL membrane (FIGS. 11Bc and 11Bd), in both surface of VICRYL membrane with collagen gel (FIGS. 11Be to 11Bh) and VICRYL membrane (FIGS. 11Bi to 11Bl). Scale bar=10 and 2 μm.

DETAILED DESCRIPTION

Figure 2A:
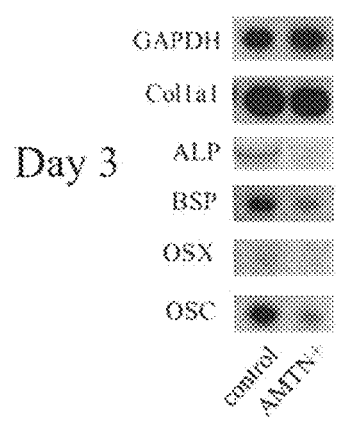
FIGS. 2A to 2D show RT-PCR results of bone markers in MC3T3-E1 mineralizing cultures with or without 100 μg/ml rh-AMTN in their media. Data is presented for day 3 (FIGS. 2A, 2B) and day 10 (FIGS. 2C, 2D). The 2% agarose gels showing the PCR products are shown in (FIG. 2A) (3 days in culture) and FIG. 2C (10 days in culture). The corresponding quantitative RT-PCR data are shown in FIG. 2B (3 days in culture) and FIG. 2D (10 days in culture). Data was presented as mean±standard deviation; (*): mean significantly different between the groups with an unpaired t-test (* $p<0.05$ and ** $p<0.01$, n=3 experiments).

Various embodiments and aspects of the disclosure will be described with reference to details discussed below. The following description and drawings are illustrative of the disclosure and are not to be construed as limiting the disclosure. The Figures are not to scale. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

Unless defined otherwise, all technical and scientific terms used herein are intended to have the same meaning as commonly understood to one of ordinary skill in the art.

Methods

Recombinant Human Protein Production

The procedures of recombinant human (rh) AMTN protein production were previously described (Abbarin et al., 2015). Briefly, the N-terminally 6× His tagged rh AMTN protein was expressed in *E. coli* (pET-15b expression system, Novagen, Merck KGaA, Darmstadt, Germany) and affinity purified on a Ni-NTA agarose column (Qiagen, CA). The protein elute from the column was then dialyzed against 50 mM $NH_4HCO_3$ (Mallinckrodt, Mississauga, Canada), and freeze-dried (Thermo Savant ModulyoD, N.Y.). The 6× His tag was cleaved from the protein N-terminus using a thrombin cleavage kit (CleanCleave, Sigma-Aldrich, Mo.). The protein was then dialyzed against water to remove the remaining calcium salt from the thrombin cleavage buffer, freeze-dried, and stored at −80° C. before use for experiment.

Cell Culture Experiments

Mouse osteogenic cell line MC3T3-E1 subclone 14 (ATCC # CRL-2594) was grown in αMEM (without ascorbic acid—Gibco A1049001) containing 10% fetal bovine serum (FBS, Sigma F1051), 250 μg/ml Penicillin (Sigma P3032), 60 μg/ml gentamycin (Wisent 450-135-XL), and 0.25 µg/ml Fungizone (Invitrogen 15290). At 80% confluence, cells were seeded at 50,000 cells/cm2 in a 24-well plate (Falcon, 087721H). The next day (set at day 0) confluent cells were supplemented with regular αMEM containing 50 µg/ml ascorbic acid (Gibco 12571-063), as well as 3 mM sodium dihydrogen phosphate (BioShop SPM306), and 100 µg/ml rh-AMTN. Inorganic phosphate was also added to control cells. The cell media was changed every three days. Experiments were performed in triplicate. On day 10 cells were washed with D-PBS (Wisent Inc. 311-425-CL), fixed with 10% v/v formaldehyde (Sigma F8775) at room temperature for 10 minutes, and stained with 2% Alizarin red S (Sigma A-5533), as described (Gregory et al., 2004).

RNA Isolation and Real-Time PCR Analysis

Total RNA was extracted from osteoblast cells containing 100 µg/ml rh-AMTN in their media or control cells without any protein additions on days 3 and 10 and purified using the RNeasy Plus Mini kit (Qiagen 74134) and according to the manufacturer's instructions. For quantitative real-time PCR, 0.6 µl of RNA was prepared with an iTaq™ Universal SYBR Green One-Step Kit (Bio-Rad 172-5150) and reverse transcribed and amplified with mouse gene-specific primers as listed in Table 1. The RT-PCR conditions were 50° C. for 30 minutes (cDNA synthesis), 95° C. for 5 minutes (reverse transcriptase inactivation), and alternating incubations at 95° C. for 15 seconds and 60° C. for 1 minute, for 30 cycles (PCR reaction). The reaction was performed and analyzed for expression quantity in a CFX96™ thermal cycler (Bio-rad). Data were normalized relative to the control gene GAPDH. Alkaline phosphatase (ALP) expression was analyzed semi-quantitatively (Hoac et al., 2013) using primers reported previously (Addison et al., 2008). The reactions were performed in three triplicate measurements. The PCR products were then run on a 2% agarose gel stained with ethidium bromide and visualized under UV light.

TABLE 1

Mouse gene-specific primers used for RT-PCR reactions

| Gene | Forward primer 5-3' | Reverse primer 5-3' |
| --- | --- | --- |
| Collagen type Iα1 | GAGCGGAGAG TACTGGATCG | TACTCGAACG GGAATCCATC |
| BSP | GGGAGGCAGT GACTCTTCAG | TCGTCGCTTT CCTTCACTTT |
| Osteocalcin | GCGCTCTGTC TCTCTGACCT | GCGGTCTTCA AGCCATACTG |
| Osterix | TCCTCGGTTC TCTCCATCTG | TGCAGGAGAG AGGAGTCCAT |
| ALP | GGGGACATGC AGTATGAATT | GGCCTGGTAG TTGTTGTGAG |
| GAPDH | AACTTTGGCA TTGTGGAAGG | ACACATTGGG GGTAGGAACA |

RhAMTN-impregnated Collagen Gel Preparation

The collagen hydro gel polymerized by mixing the following components on ice; 6 mg/ml Bovine collagen solution type I (Nutragen®, Catalog #5010-D, Advanced BioMatrix, Calif.), 0.1M NaOH, 20 mM Genipin (G4796, Sigma, Mo.), and Dulbecco's Phosphate-Buffered Saline (DPBS, Wisent, Canada) were mixed to a final collagen gel concentration of 3.4 mg/ml. For AMTN-embedded collagen gel, the rh-AMTN protein was dissolved in DPBS to a final concentration of 580 µg/ml in the final gel product (FIG. 3A).

RhAMTN-Membrane Preparation

Figures 5A, 5B, 5C:
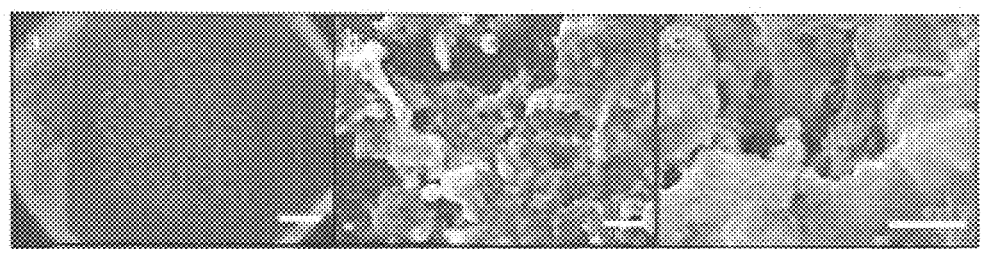
FIGS. 5A, 5B, 5C show SEM images of AMTN-treated dentin slices incubated in the SBF buffer at 37° C. for 24 hours showing calcium phosphate precipitates were seen on the surface of AMTN-treated dentin, with the magnification increasing from FIGS. 5A to 5C, Scale bar=1000, 20, 5 μm from FIGS. 5A to 5C.
Figures 5D, 5E, 5F:
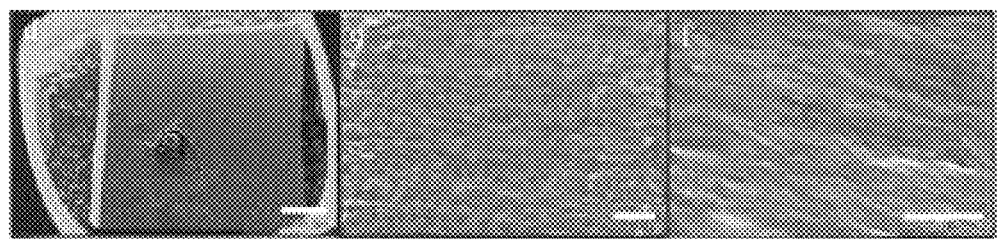
FIGS. 5D, 5E, 5F show SEM images of dentin slices incubated in phosphate buffered saline (PBS) n the absence of AMTN showing no precipitate being observed, with the same scales as FIGS. 5A to 5C.
Figures 5G, 5H, 5I:
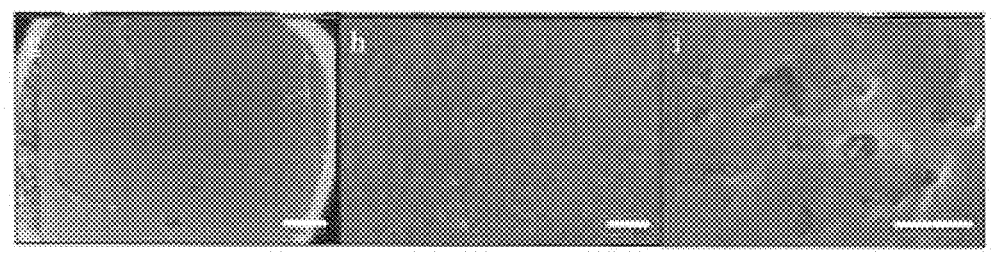
FIGS. 5G, 5H, 5I show SEM images of control dentin slices incubated in SBF buffer in the absence of AMTN, with the same scales as FIGS. 5A to 5C.

The collagen hydro gel described above was applied on the 5 mm×4 mm CYTOPLAST® RTM Collagen membrane (CYTOPLAST, Collagen Matrix Inc., NJ) or Vicryl® mesh membrane (VICRYL, Ethicon, Ohio) and incubated at 37° C. for 30 minutes in a humidified incubator. Further, the collagen hydrogel solution with/without rh-AMTN (20.91 ug, final concentration 1160 ug/ml) was overlapped on the top and incubated at 37° C. for 16 overnight in a dried incubator. (FIG. 5A). CYTOPLAST, CYTOPLAST impregnated with collagen gel (CYTOPLAST+Collagen), CYTOPLAST with collagen gel and rh-AMTN (CYTOPLAST+rhAMTN), VICRYL, VICRYL impregnated with collagen gel (VICRYL+Collagen), and VICRYL with collagen gel and rh-AMTN (VICRYL+rhAMTN) membrane were prepared in this study.

Dentin Slice Preparation

The tusk of warthog was cut into 7 mm length, 7 mm width and 1 mm height with automatic diamond saw. The dentin slices were sterilized by gamma irradiation, etched by 30% phosphoric acid for 5 second, rinsed with water and air-dried. Then, the dentin surface was treated with 4.84 ul of DPBS with 20.91 µg of rh-AMTN and incubated in 37° C. for 2 hours in a humidified incubator. The AMTN solution was aspirated after incubation.

In Vitro Mineralization Assay

A modified simulated body fluid (SBF) buffer, described previously (Abbarin et al., 2015), was used in this assay. The sample was put to wells of a sterile non-tissue culture 24-well polystyrene plate and was incubated in SBF at 37° C. in a humidified incubator for 5 hours and 24 hours. The samples were then fixed in 4% paraformaldehyde in PBS, gold coated, and processed for secondary electron Scanning Electron Microscopy (SEM, FEI XL30 ESEM, Hillsboro, Oreg., USA) and transmission electron microscopy (TEM, FEI Tecnai™) analyses. TEM Images were taken at 200 kV using bright field and selected area electron diffraction (SAED) modes.

Pull-Off Test

The membrane was appressed to 7 mm×7 mm×1 mm dentin slice described above and incubated in SBF buffer for 5 hours and 24 hours. Samples were then removed from the buffer and glued to a plastic slide with super glue (LEPAGE® Super Glue GEL CONTROL®, Henkel, Düsseldorf, Germany). Peak adhesive tensile strength between the dentin and the membrane was measured using the digital force gauge (Series DFG55, OMEGA, Stamford, Conn.). Experiments were performed in triplicate.

Statistical Analysis

Statistical analyses were conducted using an unpaired t-test for RT-PCR analysis and a one-way ANOVA with Tukey multiple comparison test for pull-off test. All error bars represent the standard error of the mean. Differences were considered significant at P-values<0.05. All statistical analyses were performed with EZR (Saitama Medical Center, Jichi Medical University, Saitama, Japan), which is a graphical user interface for R (The R Foundation for Statistical Computing, Vienna, Austria). More precisely, it is a modified version of R commander designed to add statistical functions frequently used in biostatistics.

Results and Discussion

Rh-AMTN Promotes Mineralization in Osteoblast Cultures

Figure 2B:
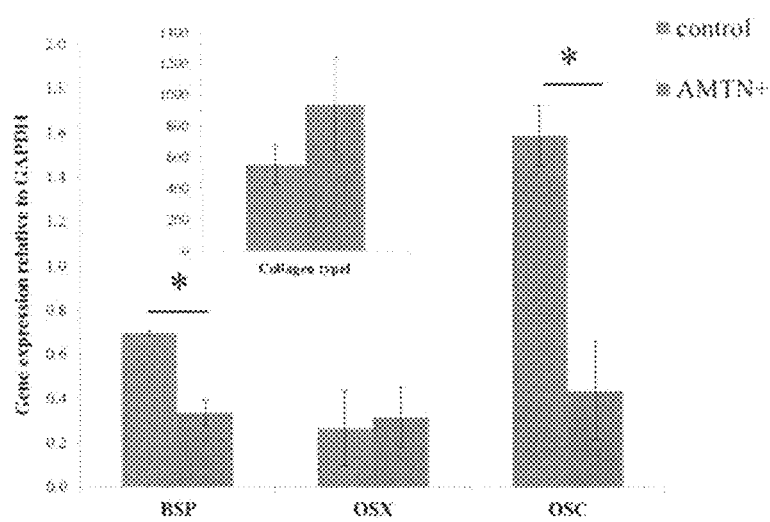
Figure 2C:
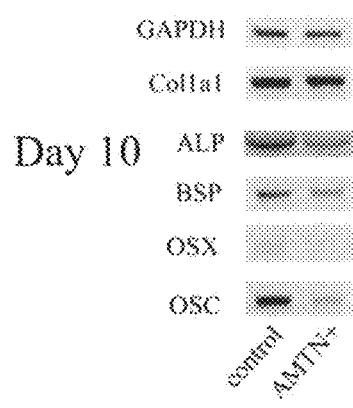
Figure 2D:
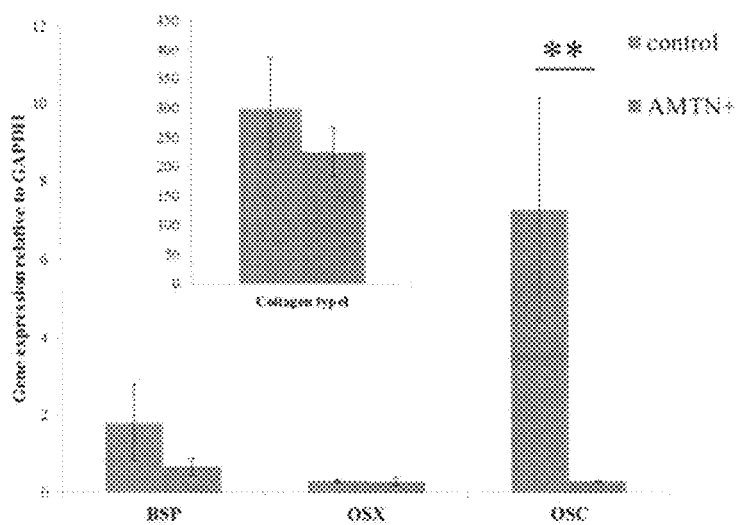

On day 10, numerous Alizarin-red stained mineralized nodules were seen in cultures supplemented with 100 µg/ml rh-AMTN (FIGS. 2A-2C), whereas control cultures remained mostly clear (FIG. D). QPCR analysis revealed that introducing rh-AMTN to the differentiating osteoblast cultures significantly down-regulates the expression of bone markers osteocalcin (OSC), alkaline phosphatase (ALP), and bone sialoprotein (BSP) at the earlier time point day 3 (FIG. 2A). Maturing osteoblasts containing rh-AMTN on day 10 also showed marked reduction in expression of OSC and ALP genes (FIG. 2C). Collagen type I (Col1a1) and osterix (OSX) expression levels were similar in control and rh-AMTN cultures at both time points.

Mineralization of AMTN-Embedded Collagen Gels

Figure 3B:
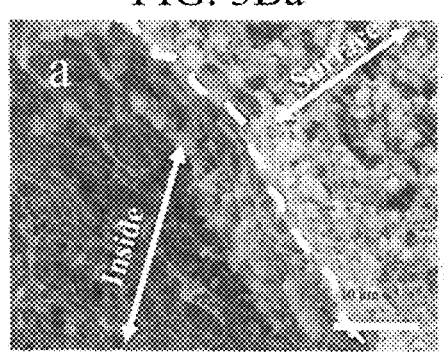
FIGS. 3Ba and 3Bb show SEMs taken at a 45 degree angle to the gel surface with FIG. 3Ba being an SEM of rhAMTN-inpregnated collagen gel and FIG. 3Bb being an SEM of collagen gel alone.
Figure 3B:
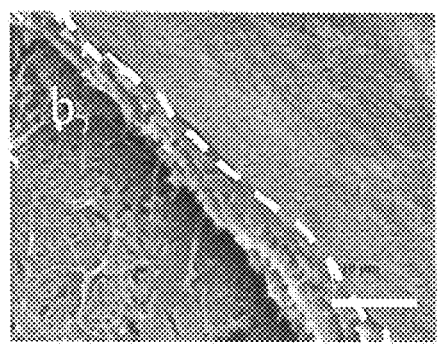
Figure 3B:
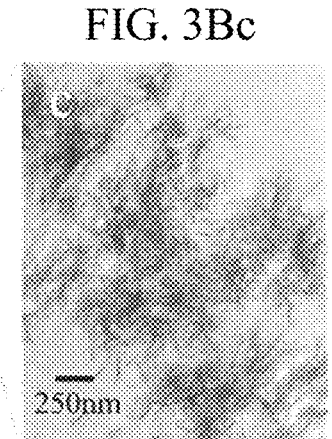
Figure 3B:
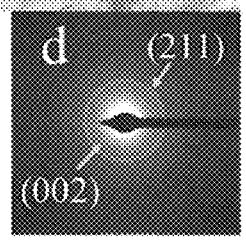

FIGS. 3Aa and 3Ab show schematic diagram of making of AMTN-impregnated collagen gel. After 5 hours of incubation in the mineralization buffer, calcium phosphate precipitates were observed on the surface of the AMTN-impregnated collagen gel. The minerals could also be observed within several micrometers deep into the gel and embedded within collagen fibers (FIG. 3Ba). TEM and SAED results revealed that these minerals were needle-like crystallites of hydroxyapatite (FIGS. 3Bc, 3Bd). No mineralization was observed in control collagen samples neither at 5 hours (FIG. 3Bb) nor even after 24 h incubation (data not shown). The buffers containing the collagen samples remained clear of any mineral deposits indicating that the observed minerals on the AMTN containing gels are not the result of any precipitation from the buffer.

Rh-AMTN Induces Mineralization on the Dentin Surface

Figures 4A, 4B, 4C:
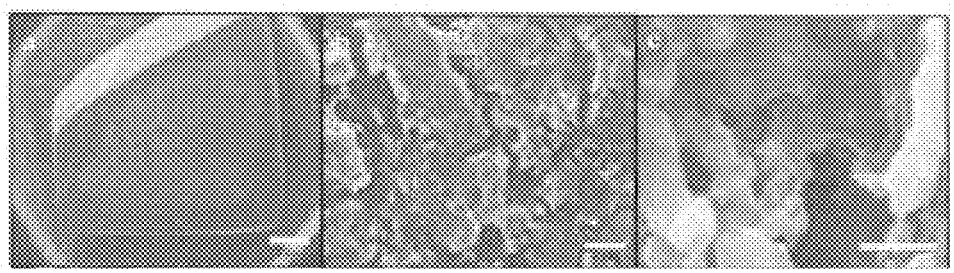
FIGS. 4A, 4B, 4C show SEM images of AMTN-treated dentin slices incubated in the SBF buffer at 37° C. for 5 hours showing calcium phosphate precipitates were seen on the surface of AMTN-treated dentin, with the magnification increasing from FIGS. 4A to 4C, Scale bar=1000, 20, 5 μm from FIGS. 4A to 4C.
Figures 4D, 4E, 4F:
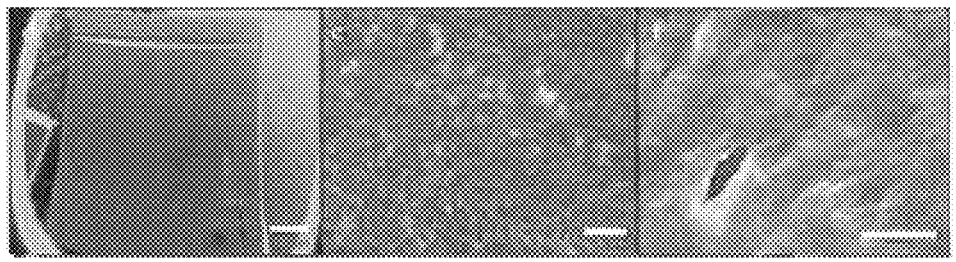
FIGS. 4D, 4E, 4F show SEM images of dentin slices incubated in phosphate buffered saline (PBS) in the absence of AMTN showing no precipitate being observed, with the same scales as FIGS. 4A to 4C.
Figures 4G, 4H, 4I:
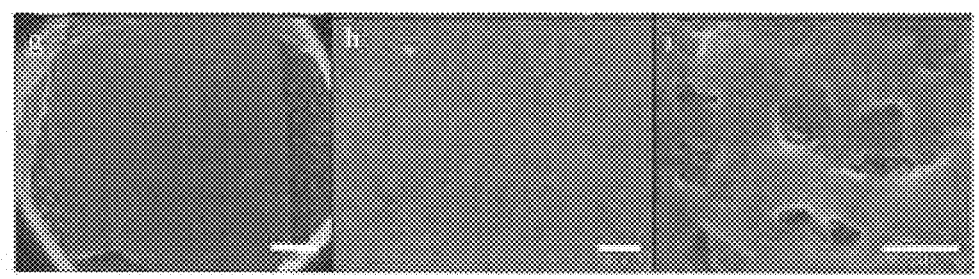
FIGS. 4G, 4H, 4I show SEM images of control dentin slices incubated in SBF buffer in the absence of AMTN, with the same scales as FIGS. 4A to 4C.

After 5 hours incubation in the SBF buffer, calcium phosphate precipitates were observed on the surface of the rhAMTN-treated dentin (FIGS. 4A to 4C). Interestingly, deposits were precipitated as if to avoid dentinal tubules and not precipitated in and on dentinal tubules (FIG. 4C). Meanwhile, no precipitate was observed in dentin treated with PBS only (no AMTN) (FIGS. 4D to 4F and FIGS. 5D to 5F) or dentin treated with SBF (no AMTN) (FIGS. 4G to 4I and FIGS. 5G to 5I) after five hours (FIGS. 4A to 4I) and even after 24 hours incubation (FIGS. 5A to 5I).

Mineralization of AMTN Membrane

Figure 6:
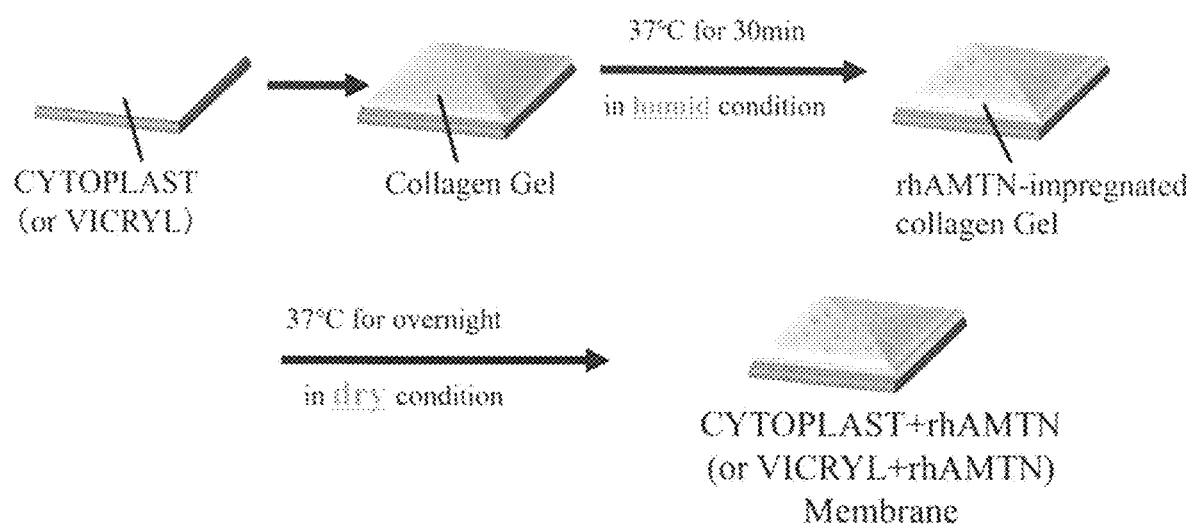
FIG. 6 is a schematic diagram of a process for producing a rhAMTN-membrane in which a collagen hydrogel solution is applied on the membrane (Cytoplast or Vicryl) and incubated at 37° C. for 30 minutes in a humidified incubator to polymerize the collagen gel within the membrane. After polymerization, a second layer of a collagen hydrogel containing rh-AMTN is applied to the top surface of the collagen-impregnated membrane and incubated at 37° C. for overnight in an incubator to polymerize the AMTN-containing top collagen layer and to desiccate the entire membrane construct.

FIG. 6 shows a schematic diagram for the fabrication of CYTOPLAST or VICRYL membranes that are first impregnated with a collagen gel (blue) and the subsequent application of a second layer of collagen gel containing rhAMTN (grey, orange dots). Once the AMTN-containing layer has gelled under humid condition, the membrane construct is dried overnight at 37° C. Such membranes were rehydrated in SBF and incubated in SBF for 5 hours (FIGS. 7Aa to 7Al) or 24 hours (FIGS. 8A to 8L). Calcium phosphate precipitates were observed only on the top (AMTN-containing) surfaces of the CYTOPLAST+rhAMTN membranes after 5 hours (FIGS. 7Aa, 7Ab) and after 24 hours (FIGS. 8A, 8B), but not on the bottom (AMTN-free) surfaces of such membranes after 5 (FIGS. 7Ac, 7Ad) or 24 (FIGS. 8C, 8D) hours. CYTOPLAST membranes without the addition of any collagen ("No additive") also showed no signs of mineral precipitation after five hours (FIGS. 7Ai to 7Al) or after 24 hours (FIGS. 8I to 8L) hours of incubation in SBF. Similar results were obtained when using VICRYL instead of CYTOPLAST membranes (not shown). Analysis of mineral deposits in cross-sections of AMTN-containing CYTOPLAST membranes by TEM also revealed that these deposits were located only at top, AMTN-containing, surface (FIGS. 7Ba, arrows), but not in the middle (FIG. 7Bb) or the bottom (FIG. 7Bc) portion of the membrane. SAED analysis of an isolated area of mineralization (FIG. 7Bd) showed diffraction patterns (FIG. 7Be inset of FIG. 7Bd) that indicate the presence of hydroxyapatite in these needle-like crystallites.

Pull-Off Test

Figure 9A:
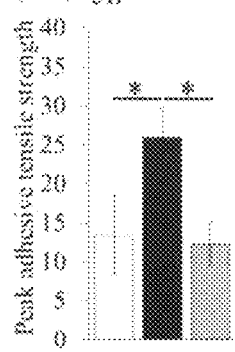
FIGS. 9A and 9B show peak adhesive tensile strength, histological and immunohistochemical analyses of CYTOPLAST+rhAMTN membranes applied to a dentin surface. Membranes were incubated in SBF buffer at 37° C. for 5 hours (FIG. 9A) and 24 hours (FIG. 9B), and then peak adhesive tensile strength between the dentin and the membrane was measured using the digital force gauge (white, CYTOPLAST membrane with 30% phosphoric acid treated dentin; black, CYTOPLAST+rhAMTN membrane with 30% phosphoric acid treated dentin; grey, CYTOPLAST membrane with 30% phosphoric acid and rhAMTN treated dentin). Data was presented as mean±standard deviation; (*): mean significantly different between the groups with a one-way ANOVA with Bonferroni multiple comparison test (* p<0.05, n=3 experiments).
Figure 9B:
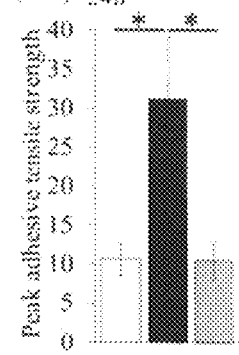
Figure 9C:
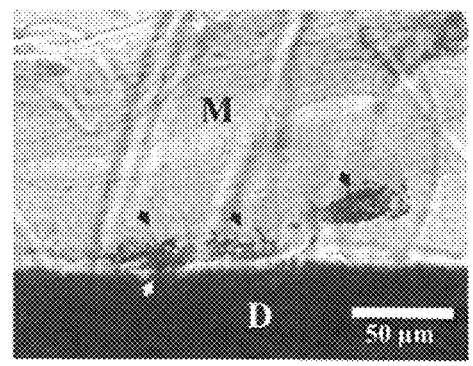
FIG. 9C shows a light microscope image of a cryosection of dentin (D) with attached CYTOPLAST+rhAMTN membrane (M), which was stained with silver nitrate solution to reveal presence of mineral and counterstained with Eosin Y to reveal collagen fibers. Mineral precipitates formed at the interface between dentin and the AMTN-containing side of the CYTOPLAST+rhAMTN membrane as pointed to by the black arrow heads. The mineralized fiber connecting membrane and dentin is pointed to by the white arrow head. Scale bar=50 μm. M; Membrane, D; Dentin.
Figure 9D:
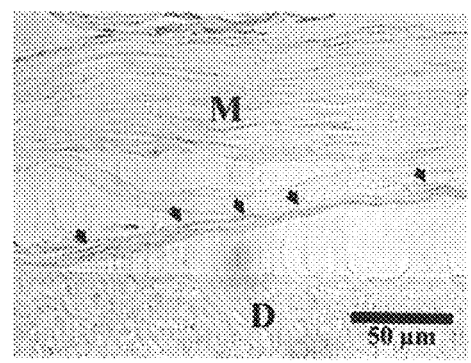
FIG. 9D shows a light microscopy image of a cryosection of dentin (D) with attached CYTOPLAST+rhAMTN membrane which was probed with antibodies against human AMTN. The most intense staining for AMTN is found at the membrane surface facing the dentin as pointed to by the black arrow heads. Scale bar=50 μm. M; Membrane, D; Dentin.

CYTOPLAST+rhAMTN and CYTOPLAST membrane were prepared, appressed to the dentin slice and incubated in SBF buffer for several hours, and then peak adhesive tensile strength between membrane and dentin was measured. CYTOPLAST+rhAMTN membrane could adhered significantly stronger to the dentin surface than CYTOPLAST membrane at 5 hours (0.52±0.07 and 0.27±0.10 kPa, respectively, p<0.05) and 24 hours (0.62±0.16 and 0.21±0.04 kPa, respectively, p<0.05) (FIGS. 9A, 9B). Interestingly, the AMTN treating to dentin surface did not improve adhesive strength of CYTOPLAST membrane to the dentin surface at 5 hours (0.24±0.06 kPa) and 24 hours (0.21±0.05 kPa). The same experiment was conducted using VICRYL. VICRYL+Collagen was used as control, because VICRYL did not stick to the dentin surface at all (data not shown). VICRYL+rhAMTN could adhered significantly stronger to the dentin surface than VICRYL+COL at 5 hours (0.41±0.05 and 0.26±0.06 kPa, respectively, p<0.05) and 24 hours (0.55±0.08 and 0.29±0.08 kPa, respectively, p<0.05) (FIGS. 10A, 10B). The AMTN treating also did not work to improve adhesive strength of VICRYL+Collagen membrane (0.23±0.07 and 0.19±0.05 kP, at 5 hours and 24 hours, respectively).

In summary, in one embodiment the present disclosure provides a product comprised of a collagen gel, prepared from commercial sources, to which recombinant human AMTN protein is added. This AMTN-collagen gel is applied to one side of commercially available scaffolds (e.g. Vicryl mesh or Cytoplast collagen membranes) that have been impregnated with AMTN-free collagen gel. In use the resulting two-layer collagen membrane (layer 1 comprised of scaffold surrounded by collagen gel; layer 2 (on top of layer 1) which is comprised of collagen gel containing AMTN) is applied to a mineralized tissue surface (e.g. dentin, bone) with the collagen gel containing AMTN of layer 2 facing this mineral surface due to the presence of AMTN in layer 2, triggers the formation of hydroxyapatite mineral deposits that intimately connect with the existing mineral surface and thus provide physical attachment.

Devices may produced in the Amelotin protein is present in the second layer is an amount from about 5 to about 25% % by wt. in collagen solution. More preferably the Amelotin protein is present in the second layer is an amount from about 10 to about 20% by wt. in collagen solution.

There mineral surface may be a mineralized tissue surface, such as dentin or bone to give some non-limiting examples. In addition, the mineralized surface is one where the mineral is hydroxyapatite, for example, the mineralized surface may be a calcium phosphate coated implant surface for dental or orthopedic implants.

Combination of AMTN and ODAM

Nucleation Assay

Figure 12A:
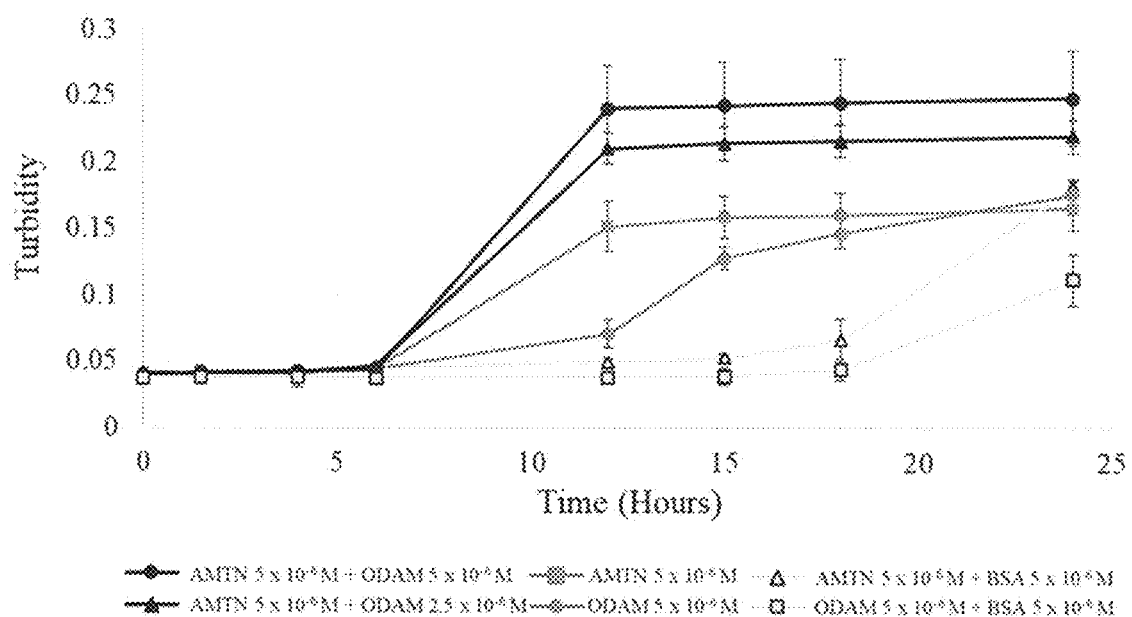
FIG. 12A shows turbidity versus time showing the light scattering results of a combination of AMTN and ODAM resulting in higher light-scattering values after about 12 hours than AMTN or ODAM alone.

AMTN, ODAM and BSA were dissolved in the mineralization buffer in various combinations. The buffer was added to wells of a sterile non-tissue culture 96-well polystyrene plate (200 μL per well) and incubated at 37° C. in a humidified incubator to prevent evaporation. To monitor the kinetics of calcium phosphate mineralization, a light-scattering assay was conducted in which the clarity versus turbidity of the solution indicated the onset and extent of precipitation from the mineralization buffer influenced by the dissolved protein. The light-scattering measurements were performed in a microplate reader (Titertek Multiskan MCC/340, Labsystems, Helsinki, Finland) at 540 nm at different time points during the nucleation assay experiment. FIG. 12A shows turbidity versus time showing the light scattering results of a combination of AMTN and ODAM resulting in higher light-scattering values after about 12 hours than AMTN or ODAM alone. The results of FIG. 12A show that combination of AMTN and ODAM resulted in higher light-scattering values after about 12 hours than AMTN or ODAM, while combination of AMTN or ODAM with BSA delayed nucleation of AMTN and ODAM, indicating the synergistic effect between AMTN and ODAM.

Figure 12B:
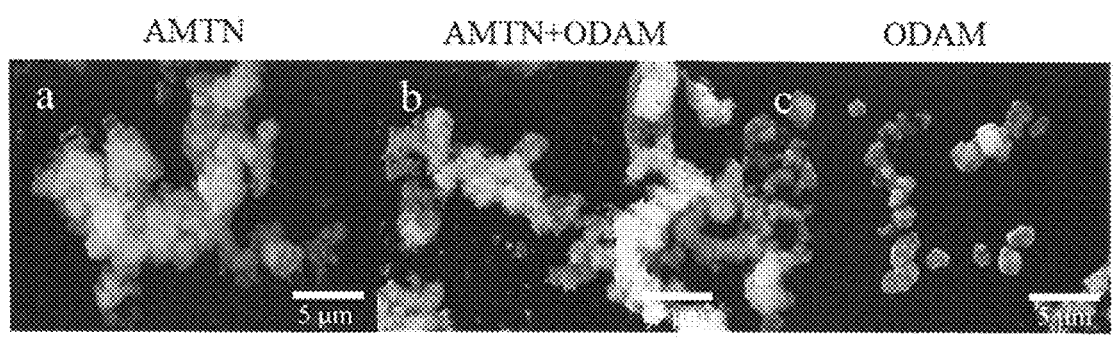
FIGS. 12Ba to 12Bc shows three SEM images with FIG. 12Ba showing AMTN precipitates only, FIG. 12Bb showing a the precipitates of a mixture of AMTN+ODAM, and FIG. 12Bc showing ODAM precipitates alone.

FIGS. 12Ba to 12Bc shows three SEM images with FIG. 12Ba showing AMTN precipitates only, FIG. 12Bb showing a the precipitates of a mixture of AMTN+ODAM, and FIG. 12Bc showing ODAM precipitates alone.

Thus, a similar product using a combination of the AMTN and the ODAM protein was observed to form hydroxyapatite mineral deposits that intimately connect with the existing mineral surface and thus provide physical attachment, albeit on a longer time scale than the AMTN product. Thus products containing both proteins also formed hydroxyapatite mineral deposits that intimately connect with the existing mineral surface and thus provide physical attachment. This combination of AMTN and ODAM induced mineralization in a synergistic manner and the mineralized deposits were identified as hydroxyapatite. These in vitro results indicate that the enamel proteins AMTN and ODAM are able to synergistically induce hydroxyapatite mineralization outside of their natural biological matrix context.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

Therefore what is claimed is:

1. A device for in vitro induction of biomineralization, comprising:
   a) a physiologically acceptable porous scaffold;
   b) said porous scaffold being impregnated with a first layer of collagen gel;
   c) a second collagen layer located on top of the first layer, said second layer including a mixture of collagen and Amelotin protein (AMTN), the Amelotin protein being present in the second collagen layer is an amount from about 5 to about 25% % by wt. in collagen solution; and
   d) wherein in use said device is configured to be applied with said second layer with the mixture of collagen gel containing Amelotin protein in physical contact with a mineralized tissue surface, the device being characterized in that a presence of Amelotin protein in the second layer triggers the formation of hydroxyapatite mineral deposits that intimately connect the second layer with the mineralized tissue surface and thus provide physical attachment.

2. The device of claim 1, wherein the Amelotin protein is present in the second layer is an amount from about 10 to about 20% by wt. in collagen solution.

3. The device of claim 1 wherein the mineralized surface is a mineralized tissue surface.

4. The device of claim 3 wherein the mineralized tissue surface is dentin or bone.

5. The device of claim 3 wherein the mineralized surface is one where the mineral is hydroxyapatite.

6. The device of claim 5 wherein the mineralized surface is one where the mineralized surface is a calcium phosphate coated implant surface for dental or orthopedic implants.

7. The device of claim 1, wherein said physiologically acceptable porous scaffold is any one of Vicryl mesh, Cytoplast, porous collagen membranes, and mesh membranes.

8. The device of claim 1, wherein said physiologically acceptable porous scaffold is a collagen membrane.

9. A device for in vitro induction of biomineralization, comprising:
   a) a physiologically acceptable porous scaffold;
   b) said porous scaffold being impregnated with a first layer of collagen gel;
   c) a second layer located on top of the first layer, said second layer including a mixture of collagen, Amelotin (AMTN) protein and Odontogenic, Ameloblast-Associated (ODAM) protein, said Amelotin protein being present in the second layer is an amount from about 10 to about 20% by wt, and said Odontogenic, Ameloblast-Associated protein being present in the second layer is an amount from about 15 to about 30% by wt; and
   d) wherein in use said device is configured to be applied with said second layer with the mixture of collagen gel containing AMTN and ODAM proteins in physical contact with a mineralized surface, the device being characterized in that a presence of AMTN and ODAM proteins in the second layer triggers the formation of hydroxyapatite mineral deposits that intimately connect the second layer with the mineralized surface and thus provide physical attachment.

10. The device of claim 9, wherein the mineralized surface is a mineralized tissue surface.

11. The device of claim 10 wherein the mineralized tissue surface is dentin or bone.

12. The device of claim 10 wherein the mineralized surface is one where the mineral is hydroxyapatite.

13. The device of claim 12 wherein the mineralized surface is one where the mineralized surface is a calcium phosphate coated implant surface for dental or orthopedic implants.

14. The device of claim 9, wherein said physiologically acceptable porous scaffold is any one of Vicryl mesh, Cytoplast, porous collagen membranes, and mesh membranes.

15. The device of claim 9, wherein said physiologically acceptable porous scaffold is a collagen membrane.

* * * * *